(12) United States Patent
Pal et al.

(10) Patent No.: US 8,632,560 B2
(45) Date of Patent: Jan. 21, 2014

(54) SYSTEM FOR BREAKING UP THROMBI AND PLAQUE IN THE VASCULATURE

(75) Inventors: Dharmendra Pal, Wilmington, MA (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1590 days.

(21) Appl. No.: 11/502,310

(22) Filed: Aug. 10, 2006

(65) Prior Publication Data

US 2007/0037119 A1 Feb. 15, 2007

Related U.S. Application Data

(60) Provisional application No. 60/707,396, filed on Aug. 11, 2005.

(51) Int. Cl.
*A61B 17/32* (2006.01)
(52) U.S. Cl.
USPC ............................. 606/169; 433/119; 604/22
(58) Field of Classification Search
USPC ............ 606/127, 159, 180, 200; 604/22, 104
See application file for complete search history.

(56) References Cited

U.S. PATENT DOCUMENTS

| | | | | |
|---|---|---|---|---|
| 4,040,414 A | * | 8/1977 | Suroff | ................................ 601/2 |
| 4,646,736 A | | 3/1987 | Auth | |
| 5,100,423 A | | 3/1992 | Fearnot | |
| 5,383,460 A | * | 1/1995 | Jang et al. | ...................... 600/439 |
| 5,474,530 A | * | 12/1995 | Passafaro et al. | ............... 604/22 |
| 6,165,199 A | | 12/2000 | Barbut | |
| 6,524,323 B1 | | 2/2003 | Nash et al. | |
| 6,569,147 B1 | * | 5/2003 | Evans et al. | ................... 604/509 |
| 6,629,953 B1 | | 10/2003 | Boyd | |
| 2001/0031981 A1 | | 10/2001 | Evans et al. | |
| 2002/0058904 A1 | | 5/2002 | Boock et al. | |
| 2002/0173819 A1 | | 11/2002 | Leeflang et al. | |
| 2003/0212389 A1 | | 11/2003 | Durgin et al. | |
| 2003/0212390 A1 | | 11/2003 | Chen et al. | |

FOREIGN PATENT DOCUMENTS

WO WO 2004/066852 A2 8/2004

OTHER PUBLICATIONS

2003 International Society of Endovascular Specialists article pp. 1039-1045 entitled "Filter Devices for Cerebral Protection During Carotid Angioplasty and Stenting" by Karthikeshwar Kasirajan, MD; Peter A. Schneider, MD, and K. Craig Kent, MD.

* cited by examiner

*Primary Examiner* — Corinne M McDermott
*Assistant Examiner* — Son Dang
(74) *Attorney, Agent, or Firm* — Brinks Gilson & Lione

(57) ABSTRACT

A system includes a generator with a grinder subgenerator and an ultrasonic subgenerator, a grinder handpiece, and an ultrasonic handpiece. The grinder handpiece is connected in electrical communication with the grinder subgenerator. The grinder handpiece includes a motor and a grinding tool connected mechanically to the motor. The rotational speed of the grinding tool is associated with electrical energy provided by the grinder subgenerator to the motor. The ultrasonic handpiece is connected in electrical communication with the ultrasonic subgenerator. The ultrasonic handpiece includes a transducer and a ball tip connected mechanically to the transducer. The amplitude of the vibrations at the ball tip is associated with electrical energy provide by the ultrasonic subgenerator to the transducer.

19 Claims, 4 Drawing Sheets

SYSTEM FOR BREAKING UP THROMBI AND PLAQUE IN THE VASCULATURE

CROSS-REFERENCE TO RELATED APPLICATIONS

This application claims the benefit of U.S. Provisional Application No. 60/707,396, filed on Aug. 11, 2005, entitled "SYSTEM FOR BREAKING UP THROMBI AND PLAQUE IN THE VASCULATURE," the entire contents of which are incorporated herein by reference.

BACKGROUND

The present invention generally relates to medical devices. More specifically, the invention relates to a system for breaking up thrombi or plaque in a body vessel.

It is commonly known that constrictions in blood vessels can lead to heart problems and strokes. As a result, patients are generally advised to exercise and to maintain a proper diet to avoid these debilitating diseases. Nonetheless, opening constricted blood vessels has been a problem to the medical profession for many years. It has been proposed that catheters provided with rigid dilator devices or balloon dilators or heated balloon dilators be inserted in blood vessels to enlarge the fluid passageway in constricted blood vessels. Others have proposed the use of ablation catheters provided with a cutting device having one or more cutting edges to cut and separate the matter causing the obstruction from the wall of the blood vessel. Yet others have proposed using scoring devices to remove the matter. However, any of the aforementioned devices may cause physical trauma to the blood vessel.

Ultrasonic assisted medical procedures have been performed, for example, in liposuction to remove adipose tissue from humans or other animals. These procedures tend to be less traumatic to the patient than those employing a cutting tool such as a scalpel. The ultrasonic medical procedure is typically conducted using an ultrasonically vibrating cannula extending through a portal to a surgical site. The surgeon carefully manipulates the vibrating cannula to treat tissue to be removed while avoiding other bodily tissue such as muscles and body organs.

SUMMARY

The present invention provides a system to remove thrombi or plaque from a body vessel. The system includes two components. The first component is a mechanical grinding tool that grinds away the thrombus or plaque, and the other component is a ultrasonic device that generates ultrasonic vibrations at a ball tip to liquefy or to break up the thrombus or plaque.

In a general aspect of the invention, the system includes a generator with a grinder subgenerator and an ultrasonic subgenerator, a grinder handpiece, and an ultrasonic handpiece. The grinder handpiece is connected in electrical communication with the grinder subgenerator. The grinder handpiece includes a motor and a grinding tool connected mechanically to the motor. The rotational speed of the grinding tool is associated with electrical energy provided by the grinder subgenerator to the motor. The ultrasonic handpiece is connected in electrical communication with the ultrasonic subgenerator. The ultrasonic handpiece includes a transducer and a ball tip connected mechanically to the transducer. The amplitude of the vibrations at the ball tip is associated with electrical energy provide by the ultrasonic subgenerator to the transducer.

The grinder subgenerator and the ultrasonic subgenerator may be activated by switches on the respective handpieces. The amount of electrical energy provided each subgenerator may be controlled by switches on the generator or by switches on the respective handpieces. The system may include a foot controller to activate each subgenerator.

Further features and advantages will be apparent from the following description and from the claims.

BRIEF DESCRIPTION OF THE DRAWINGS

FIG. 3b is an exploded view of the assembly of FIG. 3a;

DETAILED DESCRIPTION

Figure 1:
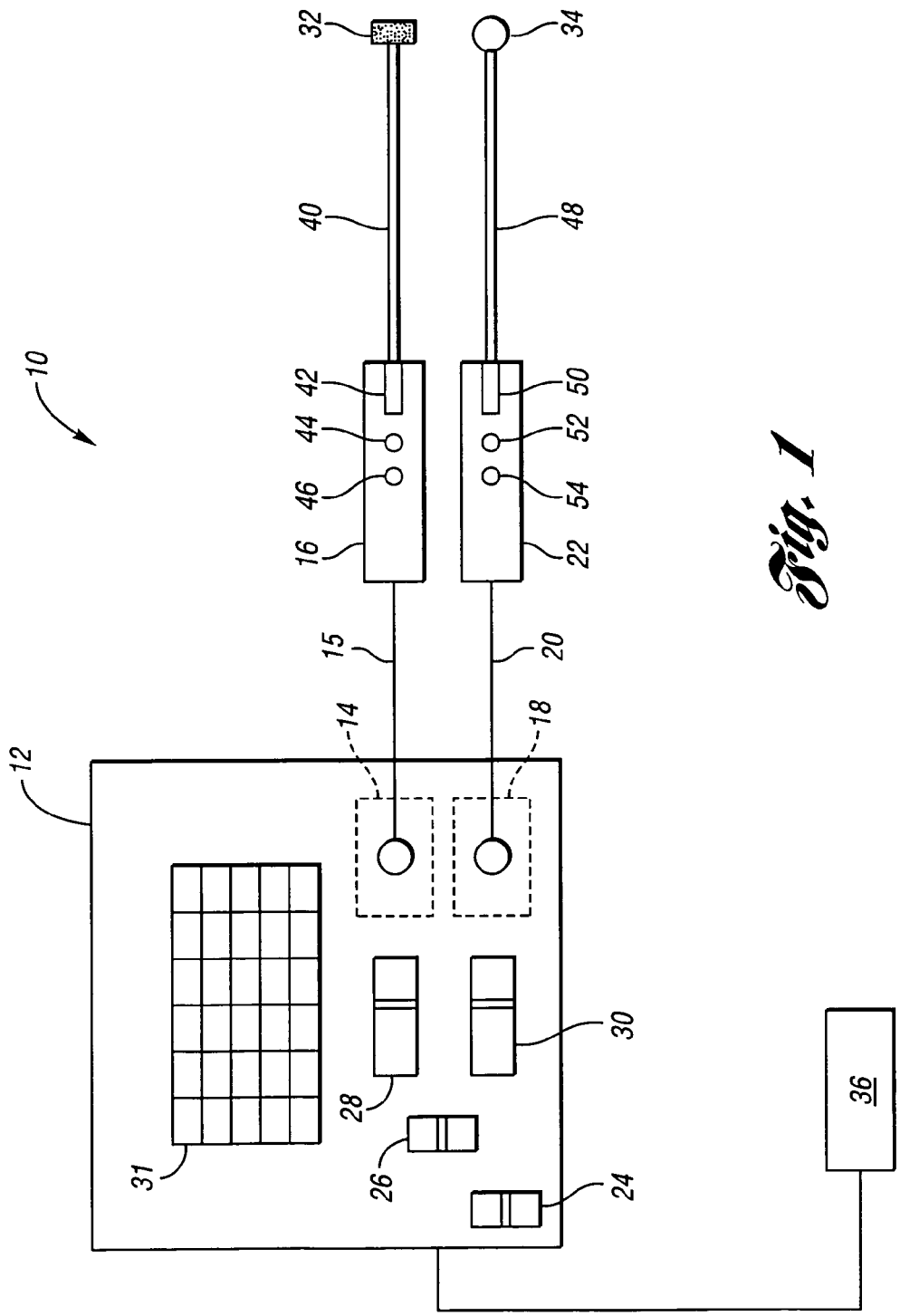
FIG. 1 illustrates a system for breaking up thrombi and plaque in a body vessel in accordance with an embodiment of the invention.

Referring now to FIG. 1, a system embodying the principles of the present invention is illustrated therein and designated at 10. The system 10 includes a generator 12 with a grinder subgenerator 14 connected in electrical communication through a control line 15 to a grinder handpiece 16 and an ultrasonic subgenerator 18 connected in electrical communication through a control line 20 to an ultrasonic handpiece 22.

The generator 12 also includes an on/off switch 24, a selection switch 26, a grinder speed control switch 28, an ultrasonic amplitude control switch 30, and a screen 31. The practitioner, such as a physician, turns the system on or off with the on/off switch 24 and selects the use of either the grinder handpiece 16 or the ultrasonic handpiece 22 with the use of the selection switch 26. Once the desired device is selected, the physician controls the rotational velocity of a grinding tool 32 associated with the grinder handpiece 16 with the grinder speed control switch 28, or the ultrasonic amplitude of the vibrations at a ball tip 34 associated with the ultrasonic handpiece 22 with the ultrasonic amplitude control switch 30. The physician can observe the performance of either device by visual inspection of the screen 31. An optional foot controller 36 is connected to the generator 12 with a control line 38, which can be employed to activate the appropriate grinder or ultrasonic component.

The grinder handpiece 16 is connected to a wire guide 40 with a lumen and includes a motor 42 connected mechanically through the lumen of the wire guide 40 to the grinding tool 32 disposed at the distal end of the wire guide 40. In operation, the grinding tool 32 is positioned in the vasculature near the location of the thrombus or plaque, and the generator 12 is then turned on. The generator 12 generates electricity through the subgenerator 14 to operate the motor 42, which in turn rotates the tool 32 to grind away the thrombus or plaque. The grinder handpiece 16 is also provided with a start/stop button 44 to control the activation/deactivation of the grinding tool 32, which can be used instead of the foot controller 36. The grinder handpiece 16 also includes a secondary grinder speed control switch 46 that the physician may use instead of the control switch 28 to control the electrical energy provided by the grinder subgenerator 14 and hence to operate the rotational velocity of the grinding tool 32.

The ultrasonic handpiece 22 is connected to a wire guide 48 to which the ball tip 34 is attached. The ultrasonic handpiece 22 also includes a transducer 50 that transforms electrical energy supplied by the generator 12 through the ultrasonic subgenerator 18 to mechanical energy in the form of ultrasonic vibrations. The vibrations travel through the wire guide 48 to the ball tip 34. Thus, when the ball tip 34 is positioned in the vasculature near a clot or plaque, ultrasonic vibrations are transmitted along the wire guide 48 as longitudinal waves. Energy is dissipated from the tip 34 as longitudinal, and transverse, compression and rarefaction waves are generated from the tip. These waves impact the thrombus or plaque to liquefy or desolve the thrombus or plaque. Moreover, the tip 34 may be placed in direct contact with the thrombus or plaque such that the tip functions as a percussion instrument against the clot or plaque to break up the clot or plaque. The ultrasonic handpiece 22 is also provided with a start/stop button 52 to control the activation/deactivation of the ultrasonic transducer 50 without the use of the foot controller 36. The ultrasonic handpiece 22 also includes a secondary ultrasonic amplitude control switch 54 that the physician may use instead of the control switch 30 to vary the electrical energy provided by the ultrasonic subgenerator 18 and hence to control the amplitude of the ultrasonic vibrations produced at the ball tip 34.

In certain embodiments, the ultrasonic transducer 50 includes multiple pairs of annular ceramic disks, for example, up to 20 or more pairs of disks, made from piezoelectric crystal and an annular heat sink. The electrical energy supplied to the transducer 50 causes the ceramic disks to generate ultrasonic vibrations with a frequency between about 15 and 125 KHz, preferably 50 KHz. The heat sink withdraws heat generated from the vibrating disks to maintain the transducer 50 at a proper operating temperature.

The transducer 50 may be provide a gradient of ultrasonic vibrations of varying energy. The ultrasonic vibrations may be continuous or they may be pulsed. The transducer 50 may provide low frequency vibrations to the tip of the wire guide, for example, in the range between about 1 to 100 Hz, especially for impacting away the thrombus or plaque. Alternatively, there may be an additional transducer to provide the low frequency vibrations. A sensor may reside in the handpiece 22 that determines the optimum operating frequency for the transducer 50. The motor 42 may be a stepper motor or any other suitable motor that can rotate the grinding tool 32 up to about 10,000 rpm. The ultrasonic feature, the low frequency percussion feature, and the grinding feature may be combined in a single handpiece. That is, the tip of the wire guide may rotate as well as emit ultrasonic vibrations, or rotate and emit low frequency vibrations to remove some or all of the thrombi and plaque.

The wire guides 40 and 48 may have a diameter in the range between about 0.002 and 0.125 in. The wire guide 48 may be a cannula, a solid wire, or a combination. Instead of a ball tip, a different shape tip may be disposed at the end of the wire guide 48 to shape and direct the ultrasonic vibrations to a particular location. For example, the tip may be concave shaped to focus the ultrasonic vibrations.

Although described in association with removal of thrombus or plaque, the system 10 may be employed as an embolic protection device. That is either component of the system 10 may be employed to remove loose plaque or thrombi, rather than removing all of it.

Figure 2:
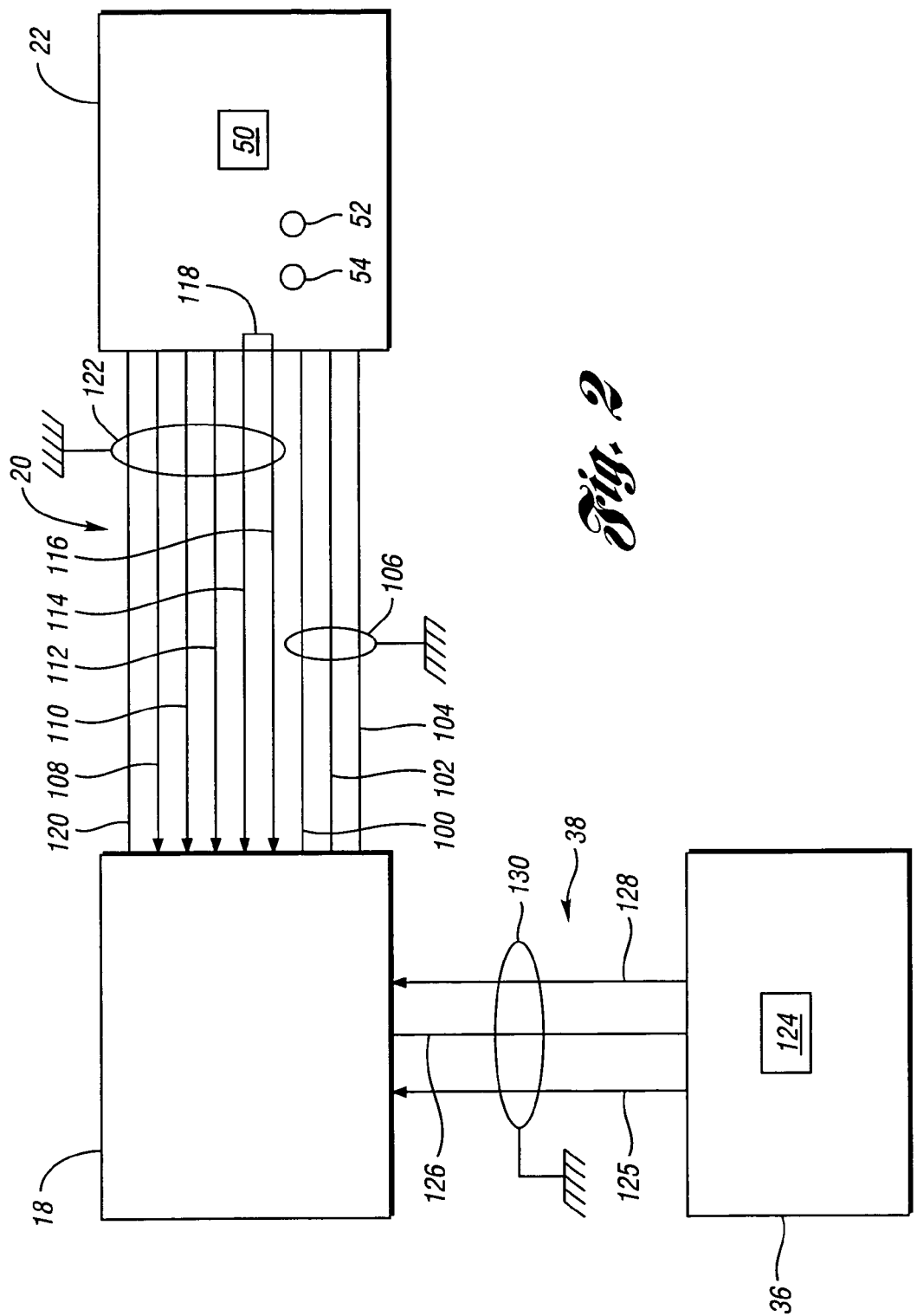
FIG. 2 is a block diagram of electrical connections of the ultrasonic component of the system of FIG. 1.

Referring now to FIG. 2, there is shown a block diagram of the electrical connections for the ultrasonic component of the system 10. A similar diagram may be used to describe the electrical connections for the grinding component of the system 10.

The control line 20 connected between the ultrasonic handpiece 22 and the ultrasonic subgenerator 18 includes a transducer power supply line 100 and two transducer ground lines 102, 104 surrounded by an electrical ground shield 106. The transducer supply line 100 transmits electrical energy from the ultrasonic subgenerator 18 to the transducer 50. The ultrasonic start/stop input signals from the start/stop switch 52 are transmitted to the ultrasonic subgenerator 18 by ultrasonic start/stop lines 108. Signals from the amplitude control switch 54 are transmitted to the ultrasonic subgenerator 18 through amplitude increase and decrease lines 110 and 112, respectively.

Two ultrasonic handpiece ID lines 114 and 116 are connected together by a jumper 118 in the handpiece 12 to indicate to the ultrasonic subgenerator 18 that the handpiece 22 is properly connected to the subgenerator 18. An additional common line 120 connects the handpiece 22 to the ultrasonic subgenerator 18. The common line 120, the ID lines 114 and 116, the ultrasonic generator start/stop line 108, the amplitude increase and decrease lines 110 and 112 are surrounded by a ground shield 122.

The foot controller 36 includes a pedal 124 to provide control signals to the ultrasonic subgenerator 18, as well as the grinder subgenerator 14 (FIG. 1) if the grinder subgenerator is selected. If the ultrasonic component is selected, as the physician depresses the pedal 124, the ultrasonic subgenerator 18 becomes activated. The ultrasonic subgenerator 18 is deactivated by releasing pressure from the pedal 124. The control line 38 connected between the foot controller 36 and the ultrasonic subgenerator 18 includes an ultrasonic subgenerator start/stop line 125 for transmitting start/stop control signals to the ultrasonic subgenerator 18. The control line 38 also includes a common ground line 126 and a connect line 128. The connect line 128 transmits a signal from the foot controller 36 to the ultrasonic subgenerator 18 to indicate that the foot controller 36 is properly connected. The ultrasonic subgenerator start/stop line 125, the common ground line 126, and the connect line 128 are surrounded by a ground shield 130.

Figure 3A:
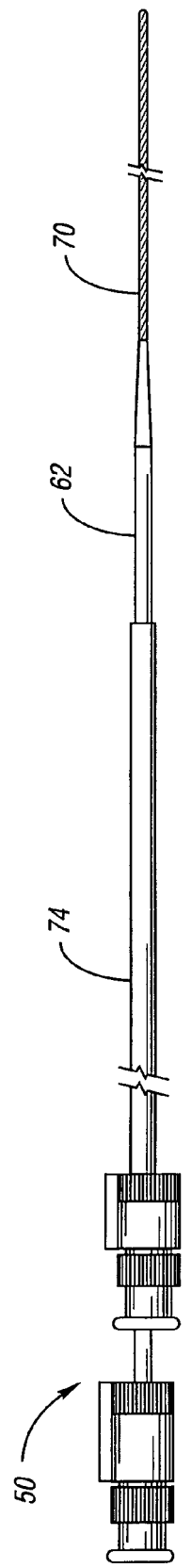
FIG. 3a is a side view of an assembly for breaking up thrombi and plaque from a body vessel.
Figure 3B:
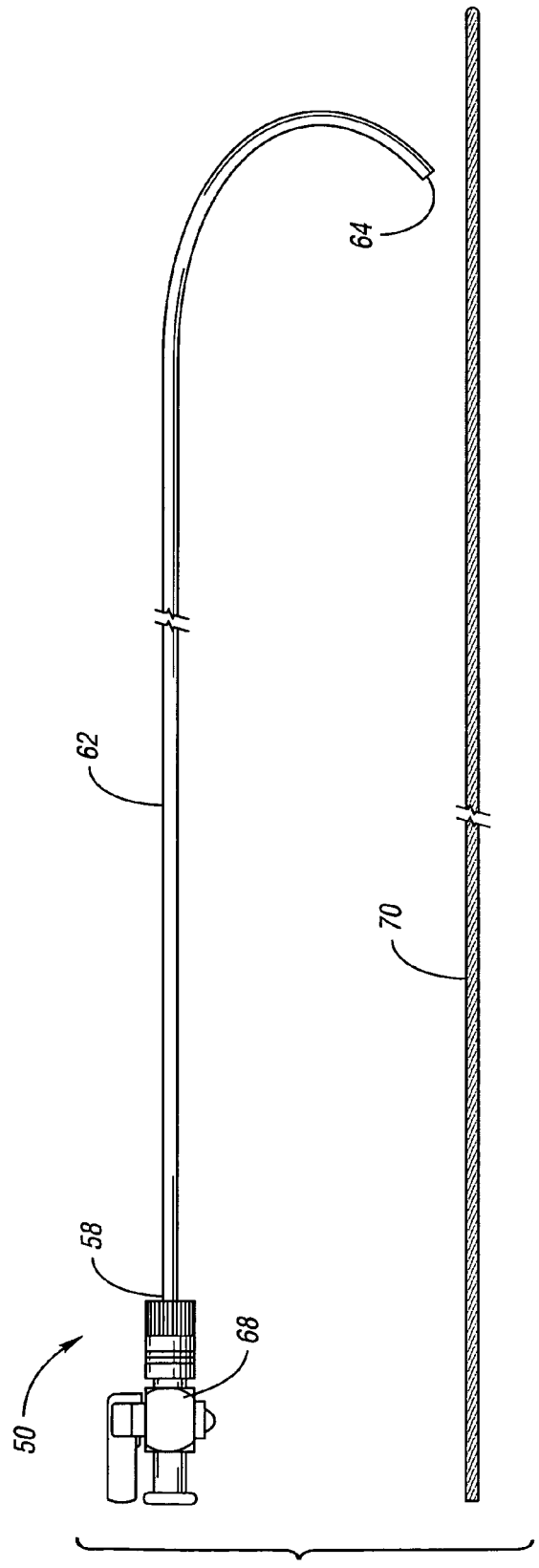

Either component of the system 10 may be used independently without any other delivery system or mechanism. Alternatively, either handpiece 16 or 22, along with the associated hardware, may be used, for example, with an assembly 50 as depicted in FIGS. 3a and 3b.

As shown, the assembly 50 includes an inner catheter 62 with a distal end 64 through which the grinding tool 32 and wire guide 40 or the ball tip 34 and wire guide 48 are positioned for deployment in the body vessel. The inner catheter 62 is preferably made of a soft, flexible material such as silicone or any other suitable material. Generally, the inner catheter 62 also has a proximal end 58 and a plastic adaptor or hub 68 to receive either component. The size of the inner catheter 62 is based on the size of the body vessel into which the catheter 62 is inserted, and the size of the wire guides 40 and 48 and the grinding tool 32 and ball tip 34. The assembly 50 may also include a wire guide 70 configured to be percutaneously inserted within the vasculature to guide the inner catheter 62 to a location adjacent an aneurism.

In use, either the wire guide 40 and grinding tool 32 or the wire guide 48 and ball tip 34 are placed in the inner catheter 62 prior to treatment of the aneurism. The grinding tool 32 or the ball tip 34 are then guided through the inner catheter preferably from the hub 72 and distally beyond the distal end 64 of the inner catheter 62 to a location within the vasculature near the clot or plaque.

The assembly 50 may include a polytetrafluoroethylene (PTFE) introducer sheath 74 for percutaneously introducing the wire guide 70, or either component, and the inner catheter 62 in a body vessel. Of course, any other suitable material may be used for the sheath 74. The introducer sheath 74 may have any suitable size, e.g., between about three-french and eight-french. The introducer sheath 74 facilitates inserting the inner catheter 62 percutaneously to a desired location in the body vessel and provides stability to the inner catheter at a desired location in the body vessel. For example, as the introducer sheath 74 is held stationary within an artery, it adds stability to the inner catheter 62, as the inner catheter 62 is advanced through the introducer sheath 74 to a desired location in the vasculature.

When the distal end 64 of the inner catheter 62 is at a location near the blockage, either the grinding tool 32 or the ball tip 34 is inserted through the inner catheter 62 and is advanced coaxially through the inner catheter 62 for deployment through the distal end 64 of the inner catheter. In this configuration, either the handpiece 16 or the handpiece 22 can be used to mechanically advance or push the grinding tool 32 or the ball tip 34.

Figure 4:
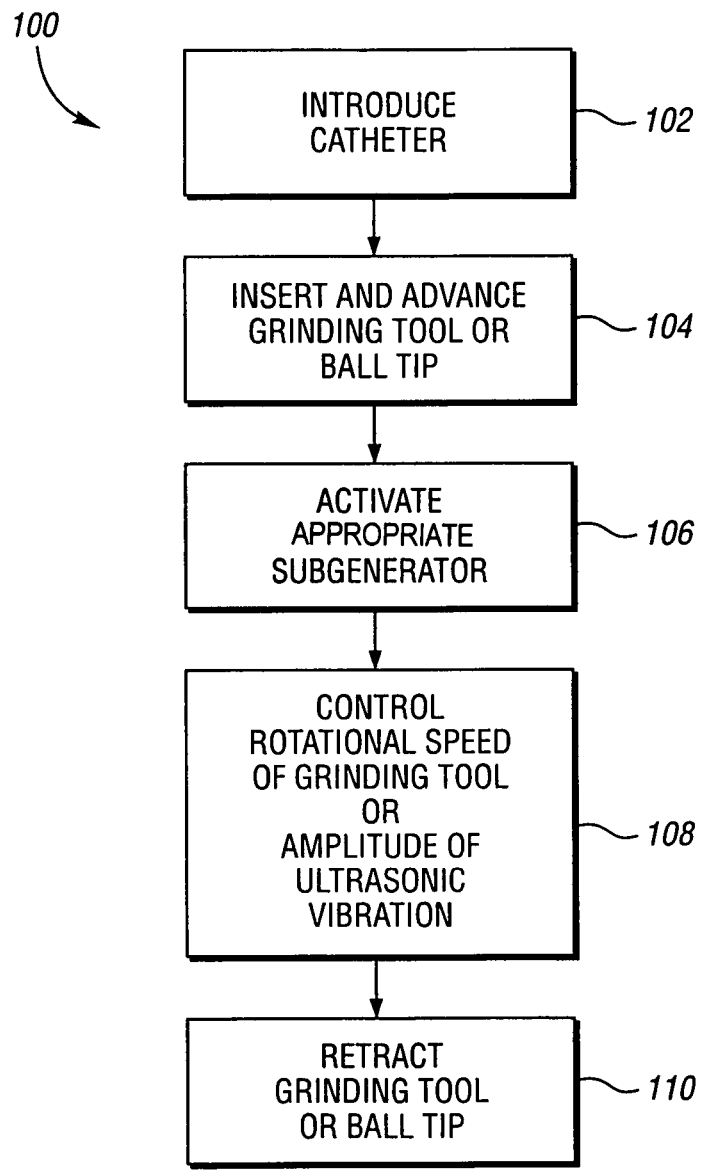
FIG. 4 is a flow chart of a sequence of steps for deploying a thrombi removal device in accordance with an embodiment of the invention.

FIG. 4 depicts a sequence of steps of a process 100 for breaking up thrombi or plaque when employing the assembly 50. In step 102, the medical practitioner, such as a physician, introduces the inner catheter 62 in a body vessel. The physician may use any suitable means, for example, fluoroscopy, to verify the placement of the inner catheter near the location of the aneurism.

Next, in step 104, either the grinding tool 32 or the ball tip 34 is placed in the inner catheter 62 and advanced beyond the distal end of the inner catheter. Once the appropriate tool is in place and the physician has selected the appropriate tool with the selection switch 26, then in step 106, the physician activates the grinder subgenerator 14 with the switch 44 or the ultrasonic subgenerator 18 with the switch 52. Alternatively, the physician can activate either subgenerator with the foot controller 36. Next, in step 108, the physician controls the rotational speed of the grinding tool 32 with the grinder speed control switch 28 or the secondary switch 46 on the grinder handpiece 16, or controls the ultrasonic vibration amplitude at the ball tip 34 with the ultrasonic amplitude control switch 30 or the secondary switch 54 on the ultrasonic handpiece 22. After the procedure is completed, then in step 110, the physician retrieves the grinding tool 32 or the ball tip 34 from the catheter 62. The physician may also retrieve the catheter 62. Optionally, the catheter 62 may remain in place for use with some alternative treatment device.

As a person skilled in the art will readily appreciate, the above description is meant as an illustration of implementations of the principles of this invention. This description is not intended to limit the scope or application of this invention in that the invention is susceptible to modification, variation and change, without departing from spirit of this invention, as defined in the following claims.

What is claimed is:

1. A system for breaking up thrombi or plaque comprising:
   a generator with a grinder subgenerator and an ultrasonic subgenerator;
   a grinder handpiece connected in electrical communication with the grinder subgenerator, the grinder handpiece including a motor and a grinding tool connected mechanically to the motor, the rotational speed of the grinding tool being associated with electrical energy provided by the grinder subgenerator to the motor;
   an ultrasonic handpiece connected in electrical communication with the ultrasonic subgenerator, the ultrasonic handpiece including a transducer, a first wire guide distally extending from the transducer, and a vibrating tip having a larger diameter than the first wire guide, the vibrating tip being located distally of the transducer attached to a distal end of the first wire guide, the vibrating tip connected mechanically to the transducer via the wire guide, the amplitude of the vibrations at the vibrating tip being associated with electrical energy provided by the ultrasonic subgenerator to the transducer, the vibrating tip being configured to contact body tissue and to liquefy, dissolve, or break up the thrombi or plaque, the vibrating tip and the grinding tool extending in non-coaxial directions relative to each other; wherein the grinder handpiece includes a second wire guide with a lumen, one end of the second wire guide being connected to the grinder handpiece, the grinding tool being disposed at the other end and being connected to the motor through the lumen of the second wire guide.

2. The system of claim 1 wherein the generator includes a selection switch for selecting the usage of either the grinder handpiece or the ultrasonic handpiece.

3. The system of claim 1 wherein the generator includes a grinding speed control switch to control the amount of electrical energy provided by the grinder subgenerator to the motor.

4. The system of claim 1 wherein the grinder handpiece includes a start/stop switch to activate/deactivate the grinder subgenerator.

5. The system of claim 1 wherein the grinder handpiece includes a secondary grinding control switch to control the amount of electrical energy provided by the grinder subgenerator to the motor.

6. The system of claim 1 wherein the generator includes an ultrasonic amplitude control switch to control the amount of electrical energy provided by the ultrasonic subgenerator to the transducer.

7. The system of claim 1 wherein the ultrasonic handpiece includes a start/stop switch to activate/deactivate the ultrasonic subgenerator.

8. The system of claim 1 wherein the ultrasonic handpiece includes a secondary ultrasonic amplitude control switch to control the amount of electrical energy provided by the ultrasonic subgenerator to the transducer.

9. The system of claim 1 wherein the ultrasonic handpiece is connected to a proximal end of the first wire guide.

10. The system of claim 1 further comprising a foot controller to activate/deactivate the grinder subgenerator or the ultrasonic subgenerator.

11. The system of claim 1 wherein the grinding tool operates with a rotational speed of about 10,000 rpm.

12. The system of claim 1 wherein the transducer generates an ultrasonic frequency in the range between about 15 and 125 KHz.

13. The system of claim 12 wherein the transducer generates an ultrasonic frequency at about 50 KHz.

14. The system of claim 1 wherein the vibrating tip is configured to be inserted into a body vessel and positioned near thrombus or plaque, the vibrating tip configured to generate waves that impact the thrombus or plaque.

15. The system of claim 1 wherein the vibrating tip is configured to be placed in direct contact with thrombus or plaque.

16. The system of claim 1, further comprising a second wire guide connecting the grinder handpiece to the grinding tool, the first wire guide connecting the ultrasonic handpiece to the vibrating tip.

17. The system of claim 1 wherein the grinding tool is movable through a catheter separately from the vibrating tip.

18. The system of claim 1 wherein the vibrating tip is configured to be inserted into the vasculature and configured to be vibrated within the vasculature to impact thrombus or plaque.

19. The system of claim 1, further comprising an inner catheter with a proximal end and a distal end, wherein the first wire guide has a length exceeding the length of the inner catheter so as to distally advance the vibrating tip through the inner catheter from the proximal end beyond the distal end of the inner catheter.

* * * * *

UNITED STATES PATENT AND TRADEMARK OFFICE
CERTIFICATE OF CORRECTION

| | | |
|---|---|---|
| PATENT NO. | : 8,632,560 B2 | Page 1 of 1 |
| APPLICATION NO. | : 11/502310 | |
| DATED | : January 21, 2014 | |
| INVENTOR(S) | : Pal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1720 days.

Signed and Sealed this
Twenty-first Day of April, 2015

Michelle K. Lee
*Director of the United States Patent and Trademark Office*